(12) United States Patent
Wang et al.

(10) Patent No.: US 7,310,149 B2
(45) Date of Patent: *Dec. 18, 2007

(54) SYSTEMS AND METHODS FOR MEASUREMENT OF PROPERTIES OF SMALL VOLUME LIQUID SAMPLES

(75) Inventors: Siqun Wang, Wilmington, DE (US); John C. Kralik, Devon, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 240 days.

This patent is subject to a terminal disclaimer.

(21) Appl. No.: 11/099,884

(22) Filed: Apr. 6, 2005

(65) Prior Publication Data

US 2006/0227326 A1    Oct. 12, 2006

(51) Int. Cl.
*G01N 21/00* (2006.01)

(52) U.S. Cl. ...................... 356/432; 356/436

(58) Field of Classification Search ............... 356/432, 356/433, 436, 439, 434, 440, 441, 442, 427; 702/22, 28

See application file for complete search history.

(56) References Cited

U.S. PATENT DOCUMENTS

| | | | | |
|---|---|---|---|---|
| 3,449,565 | A * | 6/1969 | Barringer | 250/373 |
| 4,222,670 | A * | 9/1980 | Koshiishi | 356/414 |
| 4,475,813 | A * | 10/1984 | Munk | 356/73 |
| 4,933,969 | A * | 6/1990 | Marshall et al. | 713/177 |
| 5,347,358 | A * | 9/1994 | Nebe et al. | 356/128 |
| 6,320,662 | B1 * | 11/2001 | Hafeman et al. | 356/436 |
| 6,751,632 | B1 | 6/2004 | Petrogiannis | |
| 6,937,341 | B1 * | 8/2005 | Woollam et al. | 356/436 |
| 2002/0091651 | A1 | 7/2002 | Petrogiannis et al. | |
| 2006/0061764 | A1 * | 3/2006 | Thompson et al. | 356/418 |
| 2006/0077390 | A1 * | 4/2006 | Kralik | 356/427 |

FOREIGN PATENT DOCUMENTS

WO   WO 01/42885   6/2001

OTHER PUBLICATIONS

"Agilent 8453 UV-visible Spectroscopy System—Service Manual", Agilent Technologies Deutschland GmbH, Part No. G1103-90004, Edition Feb. 2000.*
"Agilent ChemStation for UV-visible Spectroscopy Systems—Rev. A.10.0x", Agilent Technologies, Nov. 2003.*
S. Bayerbach. "A Case Study in Compliance: Supporting 21 CFR Part 11 with a UV-Vis System." Reprinted from Implementing 21 CRD Part 11 Supplement to BioPharm, Nov. 2000 (also Agilent Publication No. 5988-0949EN).
T. Klink, "Wavelength accuracy and wavelength reproducibility of the Agilent 8453 using holmium oxide solution." Agilent Publication No. 5988-9647EN, Jun. 1, 2003.

(Continued)

*Primary Examiner*—Sang H. Nguyen (57) ABSTRACT

A system for measuring properties of small volume samples includes a source of electromagnetic radiation; a first optical system; an optical delivery system; a sample holding assembly; a second optical system; a detecting system; an optical transmission system; a data collector interface component operatively connected to the detecting system; at least one processor; and at least one computer readable medium being capable of causing the at least one processor to: receive data from the detecting system corresponding to a measurement, calculate characteristics from the received data, organize the calculated characteristics in a predetermined ordering and output the organized predetermined ordering to the at least one computer readable medium.

30 Claims, 6 Drawing Sheets

OTHER PUBLICATIONS

J.C. Travis et al. "Holmium Oxide Solution as a Prototype Intrinsic Standard in Molecular Absorption Spectrophotometry." Fourth Oxford Conference on Spectrometry. A. Springsteen et al., Eds. Proc. SPIE 4826, 113-122 (2002).

J.C. Travis et al. "NIST-Traceable-Reference-Material Optical Filters Program for Chemical Spectro-photometry." Spectroscopy 14, 57-65 (Feb. 1999).

S. Bayerbach. "Content Uniformity Testing." Hewlett-Packard Publication No. 12-05963-5356E, 1995.

8453A Wavelength Accuracy Verification Test Information, Agilent Publication No. A25802.doc, 2000.

"Using Agilent ChemStation to make sure UV-visible spectroscopy data complies with FDA 21 CFR Part 11." Agilent Publication No. 5980-1051E, 2000.

"Performing the EP stray-light test with potassium chloride on UV-visible spectrophotometers." Agilent Publication No. 5988-0945EN, 2000.

Validation of CD Spectrometers. Poster (dated Oct. 2001) presented at CD 2001 8th International Conference on Circular Dichroism, Sendal (Japan) Sep. 23-28, 2001.

* cited by examiner

SYSTEMS AND METHODS FOR MEASUREMENT OF PROPERTIES OF SMALL VOLUME LIQUID SAMPLES

BACKGROUND OF THE INVENTION

Liquids (e.g., mixtures, solutions, biological samples) are often characterized using optical techniques such as photometry, spectrophotometry, fluorometry, or spectrofluorometry. Typically, a liquid is contained in a vessel referred to as a cell or cuvette, two or more of whose sides are of optical quality and permit the passage of those wavelengths needed to characterize the liquid contained therein. Recent applications require the characterization of very small liquid sample volumes. When dealing with very small sample volumes of, for example, from 1 to 2 microliters, it is difficult to create cells or cuvettes small enough to be filled and permit the industry standard 1 cm optical path to be used.

For instance, UV-Visible Spectrophotometry may be used to characterize the chemical composition of a liquid sample (in solution or suspension phase) using the absorbed spectra of the sample. The light absorbance of a sample depends on the pathlength L of light passing through the sample, as well as on the concentration of light absorbers (e.g., biomolecules, cells, etc) in a sample solution and the wavelength ($\lambda$) of light being used to characterize the sample. The wavelengths of UV-Visible light span from 200 nm to 800 nm, while ultraviolet wavelengths range from 200 to 400 nm.

UV-Visible spectrophotometry provides a convenient analysis technique to determine the concentration, purity, and integrity of a biological sample without requiring additional sample preparation other than acquiring a sample. UV-Visible Spectrophotometry measurements depend on the light source (UV lamp), the sample and sampling technique. Most biological samples absorb electromagnetic radiation at wavelengths ranging from 200 nm to 800 nm, mostly 230, 260 and 280 nm. For a DNA or RNA sample in aqueous phase, one unit of absorbance 1 Å measured at a $\lambda$ 260 nm and a pathlength of 10 mm is equal to 50/(40) ng/$\mu$l concentration.

Most biological samples are highly concentrated for downstream processing (such as microarray spotting or protein sample preparation for mass spectrometers). The absorbance of such samples can be above the saturation limit for typical spectrophotometers if the pathlength is about 10 mm. While the sample concentration range can be extended by diluting the sample, diluting sample requires additional laboratory work and can result in errors. Other approaches are needed to extend the sample concentration range that can be evaluated by the instrument.

Sampling techniques used in conventional UV-Visible Spectrophotometers include utilizing a cuvette with an optical window and fixed optical pathlength that holds a sample in a semi-closed way, direct measurement of liquid sample in a sample container (e.g., a well) along with a real-time pathlength measurement, and using a cuvetteless sample held in semi-free space between optical fibers which define a light path from a light source to a detector.

The cuvette-based sampling technique is widely used in conventional UV-Visible spectrophotometers. Generally, a sample is pipetted into a cuvette that has either a 10 mm or 2 mm path length. This technique is very limited for most biological samples since cuvettes typically used generally require a minimum 10 $\mu$l sample, which is problematic for valuable biological samples which may be present in limiting quantities, such as samples of protein or nucleic acids. A cuvette made of quartz or silica is expensive so it is typically reused after cleaning and drying. Further, adding 10 $\mu$l of sample with a pipette into a cuvette sometimes produces an air-bubble interface in the light path which can cause measurement error or void measurements. Additionally, a pathlength of 2 mm or 10 mm limits the sample concentration which may be measured to 1000 ng/$\mu$l for a DNA/RNA sample due to the limited dynamic range of absorbance of most spectrophotometers.

In one of the existing systems that enable the measurement of very small liquid sample volumes, a sample of the liquid to be examined is inserted, by means of a dispenser needle or other means, and retained between a light transmitter and a light detector. The surface tension of a microliter or submicroliter sample of liquid is used to provide sufficient means to confine the sample between two substantially parallel surfaces on anvils spaced apart a known distance; two optical fibers penetrate the parallel surfaces and provide the light for the measurement. The electromagnetic radiation emanating from the fibers is not collimated, making the determination of path length either less accurate or complicated. In order to render one of the anvils moveable, at least one of the fibers is exposed and moveable. The bending of the fiber can introduce variable optical transmission.

Based on the above, there is a need for optical instrument designs that allow for simple and accurate optical measurements.

Regulations, such as 21 C.F.R. Part 11, have been recently released and published, enabling pharmaceutical companies to provide electronic copies of their results to regulatory agencies with electronic signatures and to rely on electronic audit trails. The regulations place high emphasis on the implementation of all measures to protect and secure electronic records. These regulations cover the basic requirements of validation, limiting data access, and ensuring data integrity and data traceability. In conventional UV-visible spectroscopy data systems, it has been uncommon to find systems that support compliance with these regulations.

Therefore, there is a need for optical instrument designs that allow for simple and accurate optical measurements and which enable the compliance with electronic record-keeping regulations.

BRIEF SUMMARY OF THE INVENTION

In one aspect of this invention, a system for measuring properties of small volume liquid samples where the system design allows compliance with electronic record-keeping regulations is disclosed.

One embodiment of the apparatus of this invention of this invention includes, but is not limited to, a source of electromagnetic radiation, a first optical system for substantially collimating electromagnetic radiation, an optical delivery system capable of providing electromagnetic radiation from the source to the first optical system, a sample holding assembly capable of holding a liquid sample and placing the liquid sample in an optical path of the substantially collimated electromagnetic radiation, a second optical system capable of receiving electromagnetic radiation transmitted through the sample and at least a portion of the sample holding assembly, an optical transmission system capable of receiving electromagnetic radiation from the second optical system and transmitting the received electromagnetic radiation to a detecting system, and the detecting system for detecting electromagnetic radiation.

The above embodiment of the apparatus of this invention can also include an input system capable of providing input data, an input data interface component operatively connected to the input system and capable of receiving the input data, a data collector interface component operatively connected to the detector and capable of receiving detected data, an electromagnetic radiation source interface component capable of providing a control signal to the source of electromagnetic radiation, at least one output system, one or more processors, one or more computer readable memories having computer readable code embodied therein, the computer readable code capable of causing the one or more processors to:

receive the input data, obtain a predetermined measurement indicated by the input data;

receive detected data from the detector corresponding to the predetermined measurement, calculate predetermined characteristics from the received detected data, organize the calculated predetermined characteristics in a predetermined ordering, and output the organized predetermined ordering to the one or more computer readable memories.

In one embodiment, the computer readable code is also capable of causing the one or more processors to:

limit access to the organized predetermined ordering;

prevent modification of data and metadata corresponding to the organized predetermined ordering; and, document authorship of the organized predetermined ordering.

BRIEF DESCRIPTION OF THE DRAWINGS

For a better understanding of the present invention, together with other and further needs thereof, reference is made to the accompanying drawings and detailed description and its scope will be pointed out in the appended claims.

DETAILED DESCRIPTION OF THE INVENTION

In one aspect of this invention, an apparatus for measuring properties of small volume liquid samples where the apparatus design allows compliance with electronic record-keeping regulations is disclosed.

Figure 1:
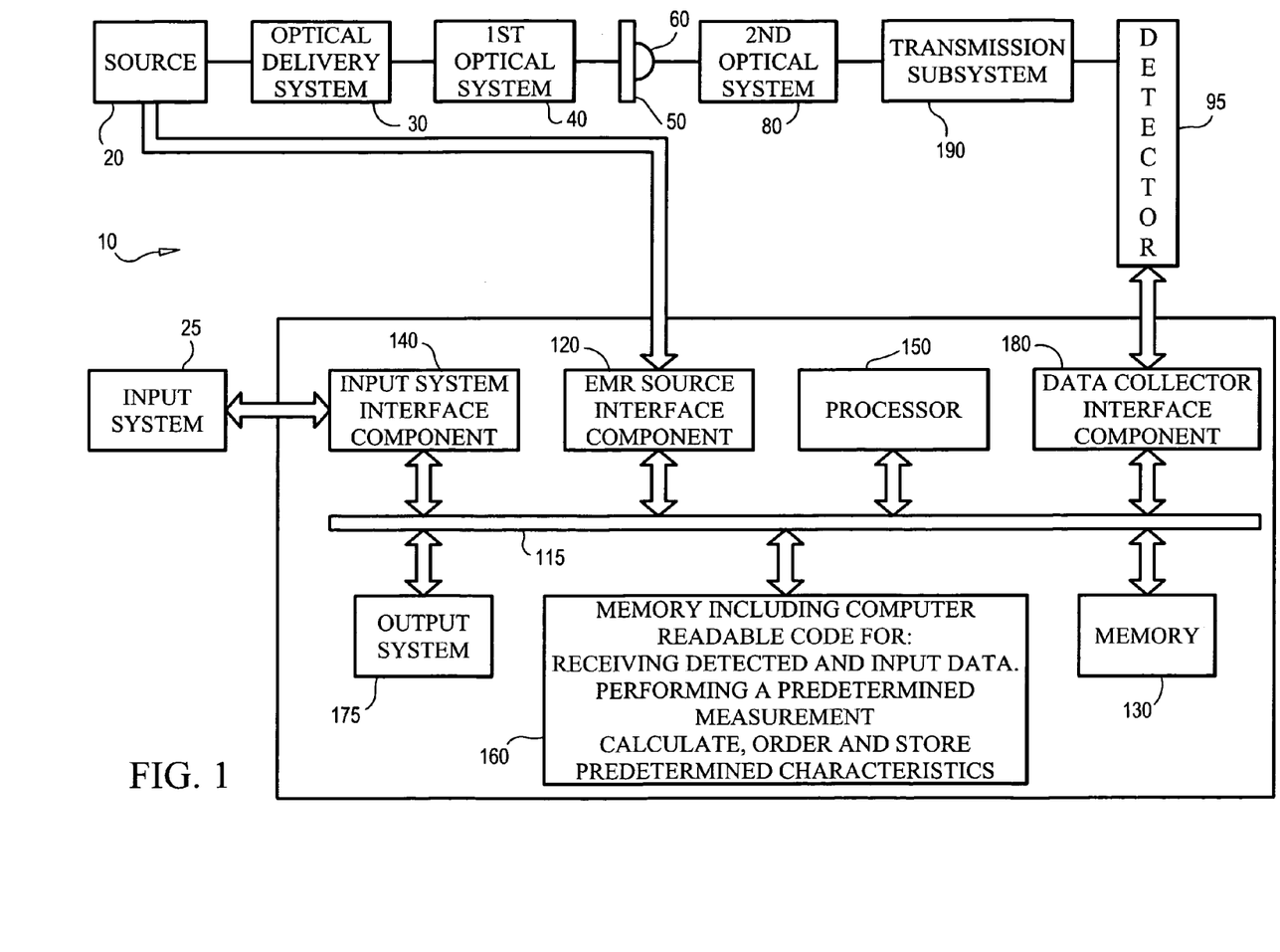
FIG. 1 is a schematic block diagram representation of an embodiment of the apparatus of this invention.

A block diagram representation of an embodiment 10 of the apparatus of this invention is shown in FIG. 1. Referring to FIG. 1, the embodiment 10 shown therein includes a source 20 of electromagnetic radiation, a first optical system for substantially collimating electromagnetic radiation 40, and an optical delivery system 30 for providing electromagnetic radiation from the source 20 to the first optical system 40. This embodiment 10 also includes a sample holding assembly 50 for holding a microvolume liquid sample 60 and placing the microvolume liquid sample 60 in an optical path of the substantially collimated electromagnetic radiation. The embodiment 10 shown in FIG. 1 also includes a second optical system 80 capable of receiving electromagnetic radiation transmitted through the sample and at least a portion of the sample holding assembly 50 and through a filter assembly 70, a detecting system 95 for detecting electromagnetic radiation, a data collector interface component 180 operatively connected to the detector 95 and capable of receiving detected data, one or more processors 150, an input system 25, capable of providing input instructions or, generally, data, operatively connected to an input data interface component 140, an output system 175, an electromagnetic radiation source interface component 120 capable of providing control information to the electromagnetic radiation source 20, one or more computer readable memories 130 (also referred to as computer usable media) having computer readable code embodied therein.

In computer enabled systems in which data is generated and stored, there are several possible system architectures. In one of the possible system architectures, both the computer readable code or instructions and the data are stored together in one or more computer readable memories. In another one of the possible system architectures, the computer readable code is stored in one or more computer readable memories and the data is stored in one or more other computer readable memories. The one or more other computer readable memories may be separate memories or partitions in a memory such as a disk drive. In the first one of the possible system architectures, the one or more computer readable memories 130 of FIG. 1 is sufficient to enable functionality of the apparatus. In the latter one of possible system architectures, the apparatus includes the one or more computer readable memories 130 of FIG. 1 and the one or more other computer readable memories 160 as shown in FIG. 1. Hereinafter, the first one of the possible system architectures is described and one or more computer memories or computer readable memories refers to the one or more computer memories 130 of FIG. 1. However, the latter one of the possible system architectures is also within the scope of this invention.

The second optical system 80 is also capable of transmitting the received electromagnetic radiation to the detecting system 95. The detecting system 95 is optically disposed to receive electromagnetic radiation from the second optical system 80. The computer readable code is capable of causing the one or more processors 150 to:

receive the input data, obtain a predetermined measurement indicated by the input data;

receive detected data from the detecting system corresponding to the predetermined measurement, calculate predetermined characteristics from the received detected data, organize the calculated predetermined characteristics in a predetermined ordering, and output the organized predetermined ordering to the one or more computer readable memories.

A "predetermined ordering" as used herein refers to the ordering of independent variables and corresponding dependent variables for each instance of a specific measurement being performed. In the embodiment in which the optical portion of the apparatus is a spectrophotometer acquiring an absorbance spectrum, the predetermined ordering comprises ordered pairs of wavelength (independent variable) and absorbance at that wavelength (dependent variable). A "specific measurement," as used herein, refers to a specific measurement that a specific apparatus is designed to perform. In the embodiment in which the optical portion of the specific apparatus is a spectrophotometer acquiring an absorbance spectrum, the specific measurement is the measurement of transmission of electromagnetic radiation through a sample. In the embodiment in which the optical portion of the apparatus is a fluorescence imaging system, the specific measurement is the measurement of the electromagnetic radiation emitted from the sample. For each embodiment of the specific apparatus and each measurement category, there is a specific measurement that the apparatus is designed to perform and a predetermined ordering dictated by the result sought.

In one embodiment, the one or more processors 150, the one or more computer readable memories 130, (the one or more other computer readable memories 160) the electromagnetic radiation source interface component 120, the output system 175, the data collector interface component 180, and the input data interface component 140 are operatively connected to each other by interconnection means 115 (a common bus, in one embodiment).

In another embodiment of the apparatus of this invention, the computer readable code is also capable of causing the one or more processors 150 to perform one or more of the following functions:

limit access to the organized predetermined ordering;

prevent modification of data and metadata corresponding to the organized predetermined ordering;

document authorship of the organized predetermined ordering; and comply with one or more other requirements of a regulation, such as, but not limited to, the requirements for electronic records and passwords set forth in 21 CFR, Part 11.

The source 20 of electromagnetic radiation can be, but is not limited to, UV/Visible LED light source, a Xenon flash lamp, or a Deuterium lamp for UV and a tungsten source for visible. An optical delivery system 30 for providing electromagnetic radiation from the source 20 to the first optical system 40 can include, but is not limited to, a fiber optic path and optical components to focus the electromagnetic radiation from the source 20 onto the fiber in one embodiment, or, in another embodiment, an optical system including discrete optical components (such as, but not limited to, lenses, prisms, or/and mirrors) for transmitting the electromagnetic radiation from the source 20. The first optical system 40 can be, but is not limited to, a plano-convex lens that collimates electromagnetic radiation and directs it through the sample holding assembly 50 and the sample 60 or a collimating optical system to perform the same function. In some embodiments, the first optical system 40 can include optical components, such as, but not limited to, prisms or reflecting components, that redirect the collimated electromagnetic radiation. In those embodiments, the filter assembly 70 can be located within the first optical system 40 at a location wherein electromagnetic radiation is substantially collimated.

The sample holding assembly 50, in one embodiment, can include, but is not limited to, an assembly which has one or more of the following features: UV/visible transparent, abrasion-resistant, a optical-quality hydrophilic center (comprised of a material such as, but not limited to, quartz glass or polystyrene. In one aspect, the transmittance of the sample holding assembly 50 is selected to ensure that a measured signal remains within the limit of the linear absorbance range of the apparatus. In one aspect, the holding assembly 50 includes an abrasion-resistant hydrophobic surround (comprised of a material such as, but not limited to, silicone, fluorosilicone, fluorosilane, Teflon® (polytetrafluoroethylene) emulsion or Teflon® AF). In one aspect, the sample (e.g., a drop) is placed on a transparent center of the holding assembly 50 and substantially collimated electromagnetic radiation propagates through the transparent center and the sample. Other embodiments of the sample holding assembly 50 in which the sample is placed in an enclosed (or partially enclosed) holding assembly (such as, but not limited to, a cuvette, microcuvette or microcapillary) are possible. In one embodiment, the invention includes holding assemblies that do not substantially reflect or refract the substantially collimated electromagnetic radiation. One exemplary embodiment includes holding assemblies (such as, but not limited to, cuvettes, microcuvettes or microcapillariess) having substantially planar surfaces that are substantially perpendicular to the collimated directed electromagnetic radiation.

The second optical system 80 can be, but is not limited to, a lens that receives the electromagnetic radiation transmitted through the sample 60 and at least a portion of the sample holding assembly 50 and through the filter assembly 70 and couples the received electromagnetic radiation onto the optical transmission system 90. The optical transmission system 90, capable of receiving electromagnetic radiation from the second optical system 80 and transmitting the received electromagnetic radiation to the detecting system 95, can include, but is not limited to, a fiber optic path and optical components to image the transmitted electromagnetic radiation onto the detecting system 95, or, in another embodiment, an optical system including discrete optical components for receiving/transmitting the electromagnetic radiation and imaging the transmitted electromagnetic radiation onto the detecting system 95. The detecting system 95 can include, but is not limited to, photodiodes (one or more), diode array detectors and, depending on the desired measurement, photovoltaic (such as photodiodes), photoconductive or photoemissive detectors.

The input system 25 can be, but is not limited to, a keyboard, a magnetic or optical disk drive or similar rotating memory device, a tape drive, another computer system, a voice input device, or an electronic tablet. The operative connection can be, but is not limited to, a wired, wireless, or network connection or a combination thereof. Embodiments of the output system 175 include, but are not limited to, solid state memories, a magnetic or optical disk drives or similar rotating memory devices, tape drives, wired or wireless connections to another computer system, printers or display devices.

The input data can include, but is not limited to, instructions to determine wavelength accuracy, wavelength stability, perform stray light tests, determine noise baseline flatness and stability or perform content uniformity tests on a certain number of samples including statistics. (For a demonstrative illustration of such measurements, see, for example, Ettore Castiglioni, CD IN EUROPEAN (AND BRITISH) PHARMACOPOEIA BENEFITS AND DRAWBACKS, presented at CD 2001 8th International Conference on Circular Dichroism, Sendai (Japan) Sep. 23-28, 2001.)

Exemplary embodiments of the measurements are given below for stray light and for wavelength accuracy and stability but this invention is not limited to those embodiments. In certain embodiments, blank samples (samples containing the diluting liquid but not the analyte of interest) are measured first. By measuring blank samples the difference in transmitted light intensity can be used to characterize the sample (containing the analyte) according to $A=-\log$ ($I/I_0$), where $I_0$ is level of transmitted light with the component being analyzed absent (blank sample), and I is the level of light transmitted through the sample and A is the absorbance value which can be related to the concentration of the component being analyzed by Beer's law.

To measure stray light, in one embodiment, a sample (also referred to as a filter) is required that absorbs all light of the wavelength at which the measurement is to be made and transmits higher and lower wavelengths. For an ideal filter, at the measured wavelength (for example, 200 nm) the transmission is 0% whereas at all other wavelengths it is 100%. In practice, cut-off filters are used which transmit all light above a certain wavelength and block all light at lower wavelengths. Salt solutions, for example, potassium chloride (e.g., 12 g/l), sodium iodide (10 g/l) and sodium nitrite (e.g., 50 g/l) in water, can be used as standard stray-light filters at 200, 220 and 340 nm respectively.

Another embodiment of a measurement performed on spectrophotometers is a determination of wavelength accuracy. In one aspect, a standard filter comprising an aqueous 4% holmium oxide solution in 10% perchloric acid can be employed to perform this measurement. The spectrum of the holmium oxide exhibits fourteen (14) transmittance bands from about 240 nm to about 640 nm. The wavelength positions of these absorbance minima are well characterized and can be used to validate the target instrument. After measuring the blank sample, the holmium oxide solution is measured a number of times. When a holmium oxide filter is used, at each measurement, a spectrum is acquired and evaluated for the fourteen (14) transmittance minima and compared against the specifications of the apparatus. The statistical evaluation of all results is used to calculate the wavelength reproducibility.

In one embodiment, the input data includes the sample or filter type (or the measurement type) and/or desired wavelength (in another embodiment the desired wavelength can be calculated or obtained from a database or table or defined by the measurement being taken). The detector data is utilized in calculating absorbance. In this embodiment, the desired ordering is in terms of wavelength and absorbance at that wavelength. The desired ordering is then outputted to one or more computer memories or output devices.

Compliance with proposed regulations requires limiting access to the outputted predetermined ordering, preventing modification of data and metadata corresponding to the organized predetermined ordering, and documenting authorship of the organized predetermined ordering.

Limiting access to the outputted predetermined ordering can be, in one embodiment, obtained by positively identifying users by having a unique user ID and a personal, secret password before being able to gain access to the outputted predetermined ordering. In one embodiment, access control is based on the user administration of the operating system (such as, but not limited to, Windows NT), which allows only users with granted permission and a proper identification to logon and perform specific actions. In one aspect, one requirement for limited system access is that only the individual users know their passwords. The implementation includes, first, setting up user identifications and appropriate permission rights for the individual users, and, second, prompting the users upon log on to the application, for the individual password.

In one aspect, the user must provide a password having a minimum password length prior to obtaining further access to data. In another aspect, a unique combination of a user ID and password is required. In a further aspect, the system accepts a password for a selected period of time, after which the password must be reset (e.g., password expiration is an aspect of the invention).

The modification of data and metadata corresponding to the organized predetermined ordering can be prevented, in one embodiment, by storing the organized predetermined ordering (processed results), the documentation of the measurements or tests performed (log books) stored in a single protected file. In that embodiment, in case of an incorrect or unreliable measurement, specific data items can be selected and a comment provided to document the reason why the data should not be considered. The selected data items are not removed from the raw data set, but stored, along with the comment in a specific data block (also referred to as "set aside"). The selected data items are still accessible and information on operator(s) accessing and/or modifying the data, time, date and reason data corresponding to the selected data items that are set aside is also stored in a protected file. Substantially accurate time and date indicators can be provided, in one embodiment, by the processor 150 and auxiliary circuits and/or software (not shown).

Documenting authorship of the organized predetermined ordering can be achieved, in one embodiment, by storing the name of the operator in the protected file. More secure documentation can be obtained by utilization of electronic signatures, that is, providing each user with a unique, secure identifier that is used to "sign" and which is protected through cryptographic techniques and through validation, such as, but not limited to, those described in WIPO International Publication No. WO0142885A1, Method And System For Generating A Secure Electronic Signature.

In one aspect, the apparatus further comprises a database which associates a level of authority with a signature. For example, the signature may be associated with a level of authority that identifies system permissions. In one aspect, the level of authority includes, but is not limited to, review, approval, authorship, and the like.

Additional control over the data may be provided by disabling access to data after a maximum number of failed entry attempts. In one aspect, access may only be re-established by a system administrator. In another aspect, access to the data is prevented after a selected interval of time during which no input to the system is provided (e.g., an inactivity timeout is provided).

In one embodiment, the apparatus provides audit trails or records of any changes made in the apparatus. The user identity and time/date of the action is recorded by the apparatus. In another embodiment, the audit trail is viewable (e.g., on the screen of a graphical user interface, accessible by one or more users of the system). In one aspect, the audit trail can be filtered. In another aspect, the audit trail is part of an encrypted database that cannot be altered. In certain aspects, the audit trail can be imported to an application for ease of viewing (e.g., such as Microsoft® Excel or Word®). In another embodiment, the apparatus may perform a check to determine that parameters for determining an optical property of a sample (e.g., such as absorbance) conform to predetermined parameters. In one aspect, the apparatus provides a report that details whether or not an approved method (following predetermined parameters) is used. In another aspect, the apparatus comprises a mechanism to lock a user interface of the apparatus to prevent unauthorized method changes before, during and/or after analysis. Authority to change parameters may be determined by confirming a password and/or user ID. In still another aspect, apparatus users can be prevented from further use of the apparatus by the apparatus in the event of failed entry attempts or by the system administrator (e.g., in the case of former employees, etc.).

In a further aspect, the apparatus performs self-diagnostic tests and may not permit additional use if one or more of the tests produces results that fail to meet predetermined standards. The self-diagnostic tests may be performed after a user provides input to the apparatus to run the test or may be automatically initiated after a predetermined number of uses of the apparatus. In one aspect, the self-diagnostic test includes evaluating one or more properties of a validated standard sample, comparing the results of the evaluation to approved results for the standard sample, and determining whether the test results deviate from the standard results by an unacceptable amount (e.g., defined by a user and/or the apparatus, based on regulatory guidelines for good laboratory practices).

Figure 2:
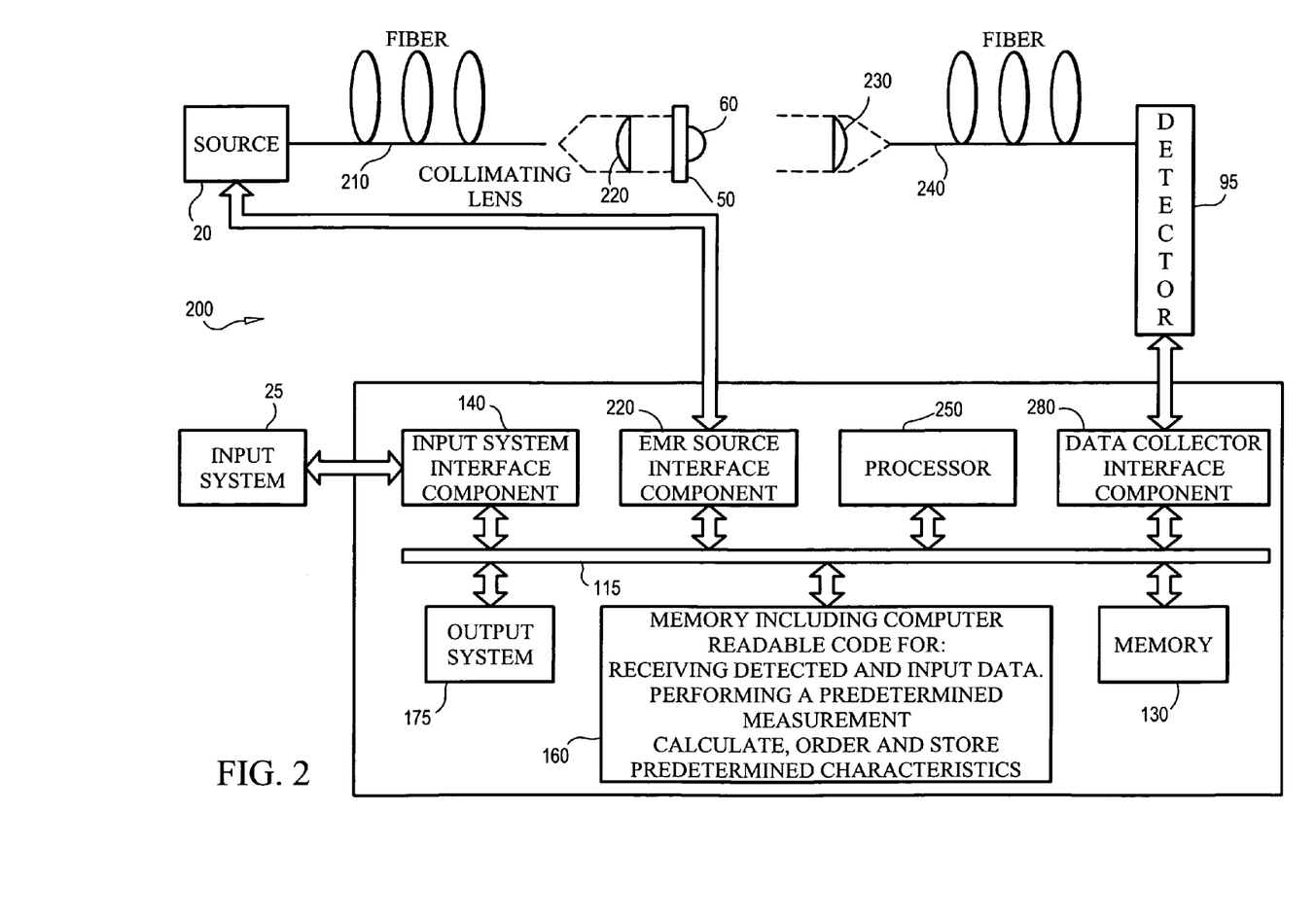
FIG. 2 is a schematic block diagram representation of another embodiment of the apparatus of this invention.

A schematic representation of another embodiment of the apparatus of this invention is shown in FIG. 2. Referring to FIG. 2, the embodiment 200 shown therein includes a source 20 of electromagnetic radiation, a first optical fiber 210 (including any optical components necessary to focus the electromagnetic radiation from the source 20 onto the fiber 210), a plano-convex lens 220 that collimates the electromagnetic radiation emanating from the fiber 210, a sample holding assembly 50 containing a sample 60, a lens 230 that receives the electromagnetic radiation transmitted through the sample 60 and at least a portion of the sample holding assembly 50, a second optical fiber 240 that receives electromagnetic radiation from the lens 230 and transmits the received electromagnetic radiation, and a detecting system 95 (where the second optical fiber 240 includes any optical components to image the transmitted electromagnetic radiation onto the detecting system 95). The first optical fiber 210 is an embodiment of the optical delivery system 30 and the second optical fiber 240 is an embodiment of the optical transmission system 90. It should be noted one or more optical fibers can be used for the same function as the first optical fiber 210 or the second optical fiber 240. In the embodiment of FIG. 2, the first optical system 40 comprises the collimating lens 220 and the second optical system comprises the lens 230 capable of receiving the electromagnetic radiation transmitted through the sample 60 and at least a portion of the sample holding assembly 50.

Figure 3:
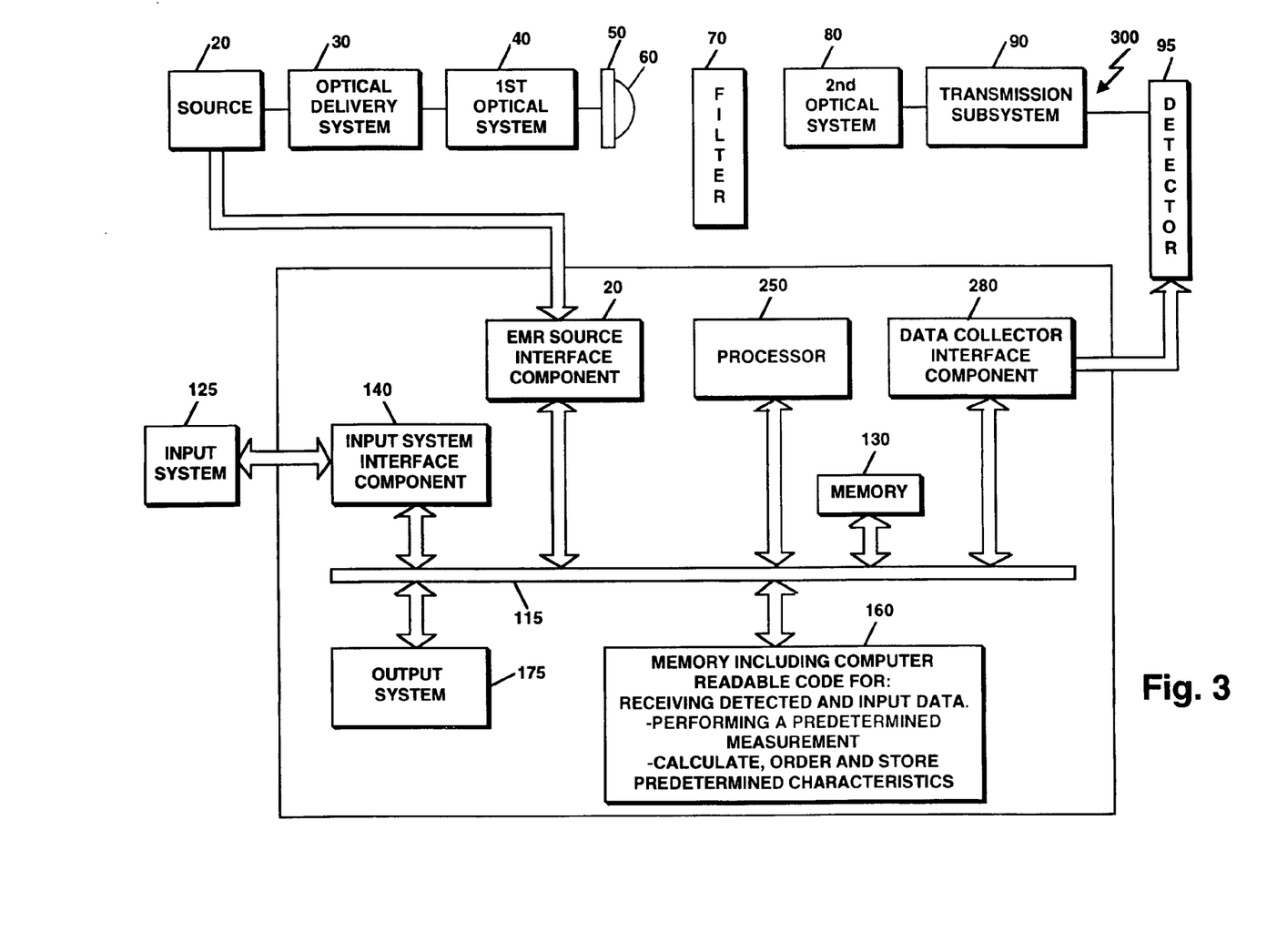
FIG. 3 is a schematic representation of yet another embodiment of the apparatus of this invention.
Figure 4:
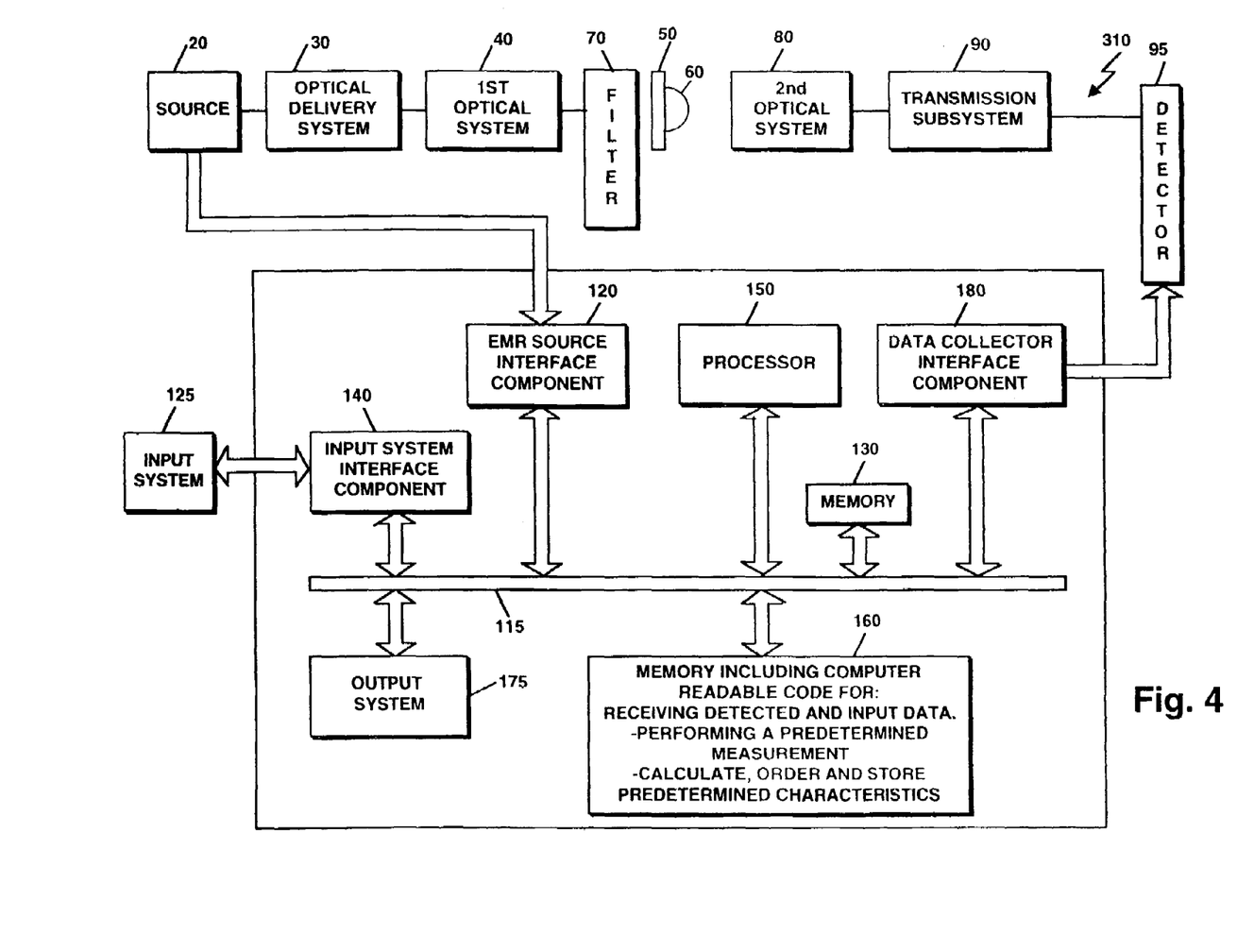
FIG. 4 is a schematic representation of a further embodiment of the apparatus of this invention.

In yet another embodiment 300 of the apparatus of this invention, shown in FIG. 3, the embodiment 300 includes a filter assembly 70 comprising one or more filters. The filter assembly is positioned in the optical path of the substantially collimated electromagnetic radiation and the substantially collimated electromagnetic radiation is transmitted through the filter assembly 70. In the embodiment 300, shown in FIG. 3, the filter assembly 70 is located between the sample holding assembly 50 and the second optical system 80. In another embodiment 310, shown in FIG. 4, the filter assembly 70 is located between the sample holding assembly 50 and the first optical system 70.

The filter assembly 70 can include one or more filters. Embodiments with more than one filter assembly are also possible. The filters in the filter assembly 70 can be, but are not limited to, conventional electromagnetic (optical) filters, liquid crystal electronically adjustable filters, or thin film dielectric continuously tunable filter. The filter assembly 70 can be integral to apparatus or can be a removable filter assembly. Likewise, filters may be integral parts of or removable from the filter assembly 70. In one embodiment in which the filter assembly 70 includes more than one filter, the filter assembly 70 can be a group of filters in a linear assembly (also referred herein as linear cartridge) or a "filter wheel." In another embodiment in which the filter assembly 70 includes more than one filter, a pre-selected filter from the filter assembly 70 may be placed in the optical path of collimated electromagnetic radiation by translating the filter assembly 70. The pre-selected filter substantially selects transmission in the pre-determined wavelength region. The filters are pre-selected based on the desired sample to be measured and the width of the spectrum of the absorption (or emission) band arising from the interaction of electromagnetic radiation and the sample. In the exemplary, but not limiting, case of biological samples, electromagnetic radiation absorption is centered at wavelengths ($\lambda$) ranging from 200 nm to 800 nm, mostly at 220, 230, 260 and 280 nm. The filter spectral band is selected to be centered at the desired wavelength and to have a width sufficient to span the width of the interaction spectral band of interest but narrow enough to exclude neighboring interaction spectral bands.

Figure 5:
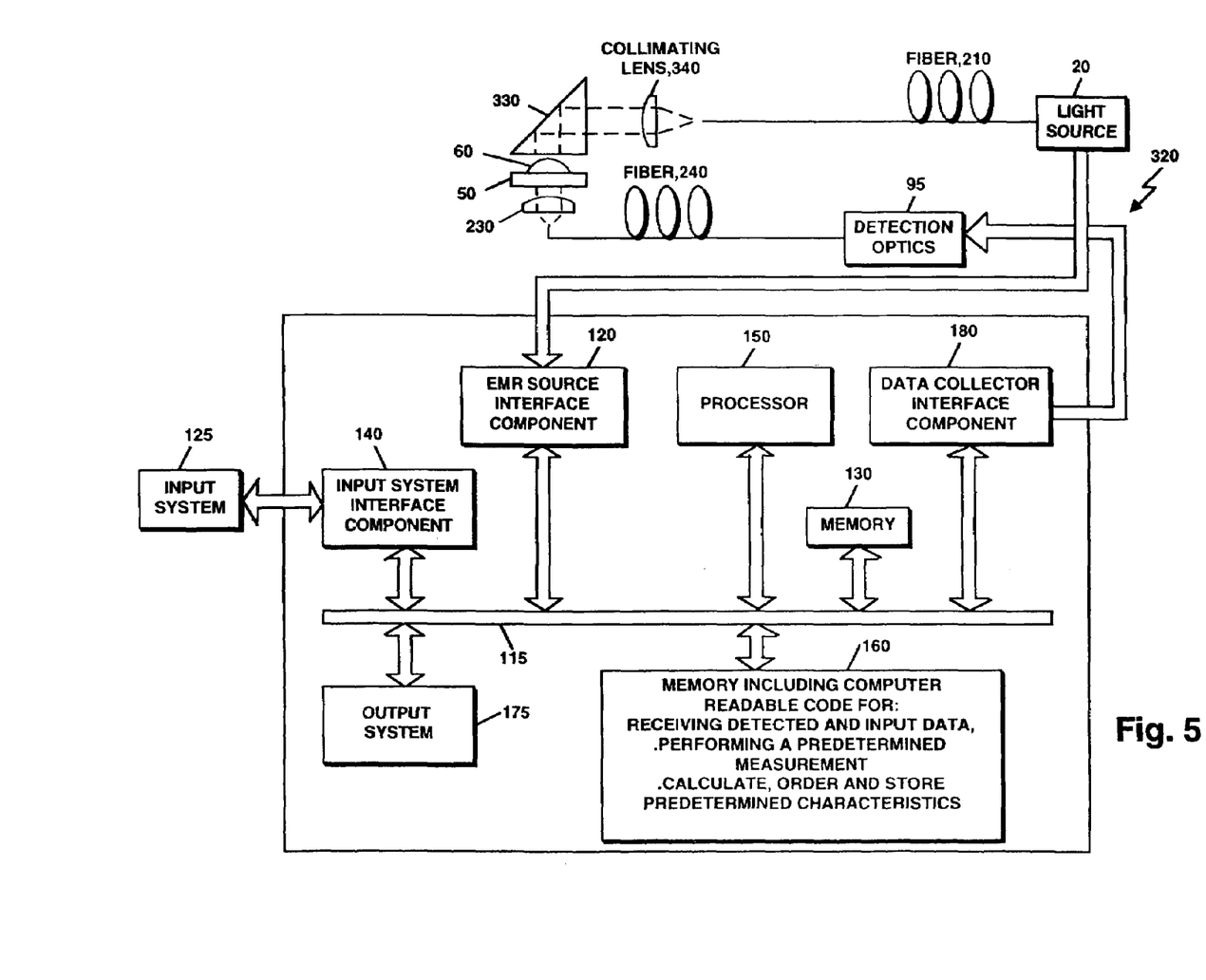
FIG. 5 is a schematic representation of still another embodiment of the apparatus of this invention.

A schematic representation of a further embodiment of the apparatus of this invention is shown in FIG. 5. Referring to FIG. 5, in the embodiment 320 shown therein, the first optical system 40 includes one or more redirecting optical components, a prism 330 in the embodiment shown, and a collimating lens 340.

Figure 6:
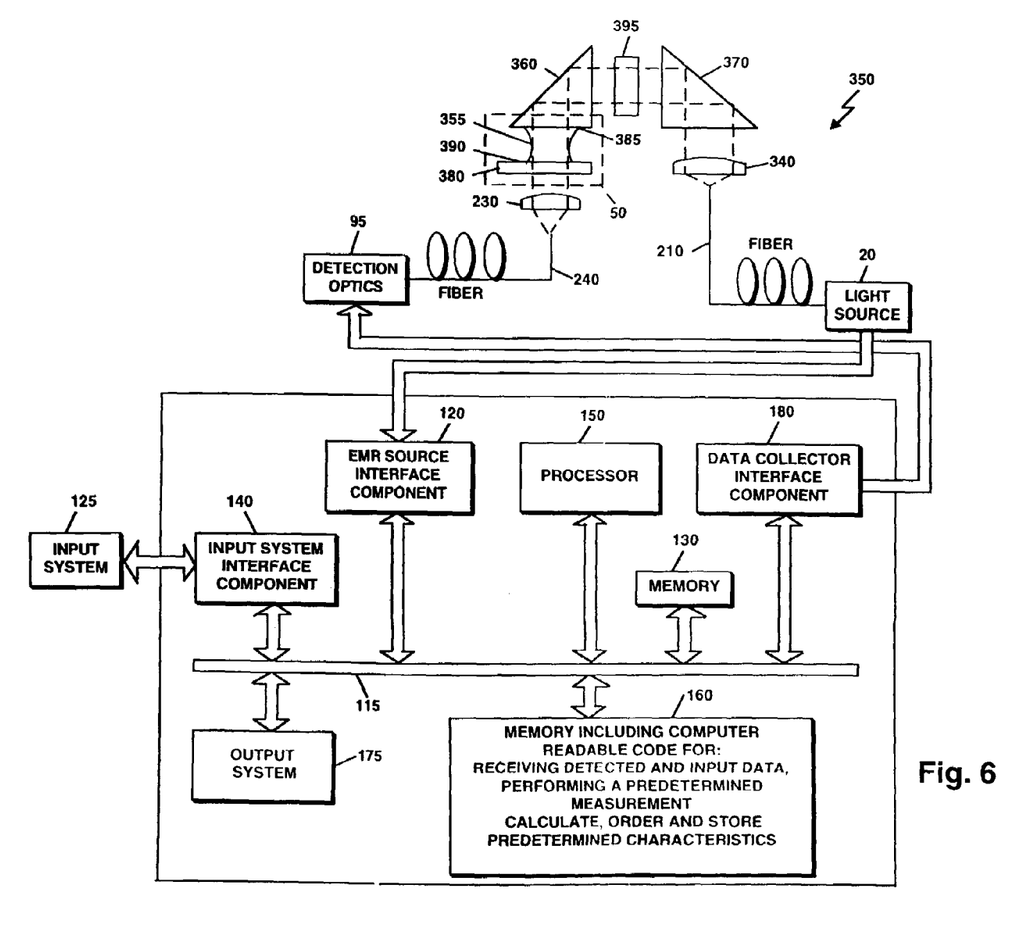
FIG. 6 is a schematic representation of still a further embodiment of the apparatus of this invention.

In the embodiment 350, shown in FIG. 6, two redirecting optical components, prisms 360 and 370 are included in the first optical system 40. In the embodiment shown in FIG. 6, a first prism 360 is optically disposed to receive the substantially collimated electromagnetic radiation transmitted through the sample 60 and at least a portion of the sample holding assembly 50. A second prism 370 is optically disposed to receive the substantially collimated electromagnetic radiation transmitted through the first prism 360. The two prisms 360, 370 are spaced apart from each other.

In the embodiment 350, shown in FIG. 6, the sample holding assembly 50 comprises a plate 380, a portion of the plate 380 being at least semi-transparent, and a surface 385 from the first prism 360, the surface 385 being spaced apart from the plate 380. The surface 385 and the plate 380 are substantially parallel to each other.

During operation of the embodiment of the apparatus of this invention shown in FIG. 6, samples are deposited onto a surface 390 of the plate 380 (the surface opposite to the surface 385 of the first prism 360) (e.g., by pipetting). The droplet when deposited, if of sufficient volume, will spread to cover at least a portion of the surface 390 of the plate 380. The surface 390 of the plate 380, onto which the drop was deposited, is brought into close proximity to the lower surface 385 of the first prism 360, making contact with the deposited droplet wetting the entire confining surface before drawing up the sample measurement column 355. The liquid sample 355 is contained by its surface tension between surfaces 390 and 385. In another embodiment of the operation, samples are loaded in two parts, one onto each of the opposing surfaces 390, 385.

In another embodiment, one of the two opposing surfaces 390, 385 can include, but is not limited to, an assembly which has one or more of the following features: UV/visible transparent, abrasion-resistant, an optical-quality hydrophilic center (comprised of a material such as, but not limited to, quartz glass or polystyrene. The transmittance of the sample holding assembly 50 is selected to ensure that a measured signal remains within the limit of the linear absorbance range of the apparatus. In one aspect, at least one of the surfaces 390, 385 of the holding assembly 50 includes an abrasion-resistant hydrophobic surround (comprised of a material such as, but not limited to, silicone, fluorosilicone, fluorosilane, Teflon® (polytetrafluoroethylene) emulsion or Teflon® AF). In one aspect, the sample (e.g., a drop) is placed on a transparent center of at least one of the surfaces 390, 385.

Also shown in FIG. 6 is a filter assembly 395 located within the first optical system 40 at a location at which electromagnetic radiation is substantially collimated. In the embodiment shown in FIG. 6, the filter assembly 395 is positioned between the two prisms 360, 370 and in the optical path of the substantially collimated electromagnetic radiation. It should be noted that other positions within the first optical system 40 at which electromagnetic radiation is substantially collimated are also possible and within the scope of this invention.

It should be noted that although several exemplary embodiments of the measurements, this application is not limited to those embodiments.

It should be noted that although one embodiment of a filter assembly located within the first optical system at a location at which electromagnetic radiation is substantially collimated was shown, other embodiments are possible and within the scope of this invention.

It should be noted that although embodiments in which the first optical system 40 includes one or more redirecting optical components and the redirecting optical components are prisms are shown above, other embodiments are possible with different redirecting optical components (such as, but not limited to, mirrors).

In general, the techniques described above may be implemented, for example, in hardware, software, firmware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to data entered using the input device to perform the functions described and to generate output information. The output information may be applied to one or more output devices.

Elements and components described herein may be further divided into additional components or joined together to form fewer components for performing the same functions.

Each computer program within the scope of the claims below may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable or usable media include, for example, a floppy disk, a flexible disk, hard disk, magnetic tape, or any other magnetic medium, a CDROM, any other optical medium, punched cards, paper tape, any other physical medium with patterns of holes, a RAM, a PROM, and EPROM, a FLASH-EPROM, any other memory chip or cartridge, a carrier wave, or any other medium from which a computer can read.

Although the invention has been described with respect to various embodiments, it should be realized this invention is also capable of a wide variety of further and other embodiments within the spirit and scope of the appended claims.

What is claimed is:

1. A measurement apparatus comprising:
   a source of electromagnetic radiation;
   a first optical system capable of substantially collimating electromagnetic radiation;
   an optical delivery system capable of providing electromagnetic radiation from said source to said first optical system;
   a sample holding assembly capable of holding a sample and placing the sample in an optical path of the substantially collimated electromagnetic radiation;
   a second optical system capable of receiving electromagnetic radiation transmitted through the sample and at least a portion of said sample holding assembly;
   a detecting system capable of detecting electromagnetic radiation;
   an optical transmission system capable of receiving electromagnetic radiation from said second optical system and transmitting the received electromagnetic radiation to said detecting system;
   said second optical system being also capable of transmitting electromagnetic radiation to said optical transmission system;
   said detecting system being optically disposed to receive electromagnetic radiation from said optical transmission system;
   a data collector interface component operatively connected to said detecting system and capable of receiving data from said detecting system;
   at least one processor; and
   at least one computer readable medium having computer readable code embodied therein, said computer readable code being capable of causing said at least one processor to:
   receive data from said detecting system corresponding to a measurement,
   calculate characteristics from the received data, organize the calculated characteristics in a predetermined ordering of independent variables and corresponding dependent variables, wherein the apparatus is designed to perform a specific measurement and the predefined ordering is dictated by the specific measurement being performed, and
   output the organized predetermined ordering to said at least one computer readable medium;
   said at least one processor, said at least one computer readable medium, and said data collector interface component operatively connected to each other.

2. The measurement apparatus of claim 1 wherein said computer readable code is also capable of causing said at least one processor to:
   limit access to the organized predetermined ordering; and
   document authorship of the organized predetermined ordering.

3. The measurement apparatus of claim 2 wherein said computer readable code is also capable of causing said at least one processor to: prevent modification of data and metadata corresponding to the organized predetermined ordering.

4. The measurement apparatus of claim 2 wherein said computer readable code is also capable of causing said at least one processor to: document authorship of the organized predetermined ordering.

13

5. The measurement apparatus of claim 4 wherein, in documenting authorship, said computer readable code is capable of causing said at least one processor to: record an electronic signature.

6. The measurement apparatus of claim 2 wherein, in outputting the organized predetermined ordering, said computer readable code is also capable of causing said at least one processor to: output a substantially accurate time and date indicator.

7. The measurement apparatus of claim 1 wherein said optical delivery system comprises at least one optical fiber; and, said optical transmission system comprises at least one other optical fiber.

8. The measurement apparatus of claim 7 wherein said first optical system comprises a collimating lens; and, said second optical system comprises a lens capable of receiving the electromagnetic radiation transmitted through the sample and the at least a portion of said sample holding assembly and coupling the received electromagnetic radiation onto said at least one other optical fiber.

9. The measurement apparatus of claim 7 further comprising: at least one filter; said at least one filter being located within said first optical system at a location wherein electromagnetic radiation is substantially collimated.

10. The measurement apparatus of claim 7 wherein said first optical system further comprises at least one redirecting optical component.

11. The measurement apparatus of claim 10 wherein said at least one redirecting optical component comprises at least one prism.

12. The measurement apparatus of claim 11 wherein said sample holding assembly comprises a plate, a portion of said plate being at least semi-transparent; and a surface from said at least one prism, said surface being spaced apart from said plate; said surface and said plate being substantially parallel to each other.

13. The measurement apparatus of claim 11 wherein said at least one prism comprises two prisms; one of said two prisms being optically disposed to receive substantially collimated electromagnetic radiation transmitted through the sample and the at least a portion of said sample holding assembly; another one of said two prisms being optically disposed to receive substantially collimated electromagnetic radiation transmitted through said one of said two prisms; said two prisms being spaced apart from each other.

14. The measurement apparatus of claim 13 further comprising: at least one filter; said at least one filter being positioned between said two prisms and in the optical path of the substantially collimated electromagnetic radiation.

15. The measurement apparatus of claim 1 further comprising: at least one filter, said at least one filter being positioned in the optical path of the substantially collimated electromagnetic radiation; the substantially collimated electromagnetic radiation also being transmitted through said at least one filter.

16. The measurement apparatus of claim 15 wherein said at least one filter is located between said sample holding assembly and said second optical system.

17. The measurement apparatus of claim 15 wherein said at least one filter is located between said sample holding assembly and said first optical system.

18. The measurement apparatus of claim 1 further comprising: an input system capable of providing input data; an input data interface component operatively connected to said input system and capable of receiving the input data; and wherein said computer readable code is also capable of causing said at least one processor to: receive the input data, obtain the measurement indicated by the input data; said at least one processor, said at least one computer readable medium, said data collector interface component, and said input data interface component operatively connected to each other.

19. The measurement apparatus of claim 1 further comprising: an electromagnetic radiation source interface component capable of providing a control signal to said source of electromagnetic radiation; said at least one processor, said at least one computer readable medium, said data collector interface component, and said electromagnetic radiation source interface component operatively connected to each other.

20. The measurement apparatus of claim 1 further comprising: at least one output system; said at least one output system operatively interconnected to said at least one processor, said at least one computer readable medium, and said data collector interface component.

21. A measurement apparatus comprising:
a source of electromagnetic radiation;
a first optical system;
said first optical system comprising at least one redirecting optical component, and a collimating lens;
an optical delivery system capable of providing electromagnetic radiation from said source to said first optical system;
said first optical system being capable of substantially collimating the provided electromagnetic radiation;
a sample holding assembly capable of holding a sample and placing the sample in an optical path of the substantially collimated electromagnetic radiation;
a second optical system capable of receiving electromagnetic radiation transmitted through the sample and at least a portion of said sample holding assembly;
a detecting system capable of detecting electromagnetic radiation;
an optical transmission system capable of receiving electromagnetic radiation from said second optical system and transmitting the received electromagnetic radiation to said detecting system; and
a filter assembly including at least one filter;
wherein a preselected filter from said at least one filter of the filter assembly is placed at a location in an optical path of the electromagnetic radiation, wherein only a predetermined wavelength region is passable through the filter, said predetermined wavelength region being centered at a desired wavelength and having a width sufficient to span a width of an interaction spectral band of interest, but narrow enough to exclude neighboring interaction spectral bands;
said second optical system being also capable of transmitting electromagnetic radiation to said optical transmission system;
said detecting system being optically disposed to receive electromagnetic radiation from said optical transmission system.

22. A method for obtaining measurements of optical properties of a sample, comprising the steps of:
placing a sample in a collimated beam of electromagnetic radiation;
obtaining at least one measurement from the interaction between the sample and the collimated beam of electromagnetic radiation;
obtaining data corresponding to the at least one measurement;
calculating characteristics from the obtained data;

organizing the calculated characteristics in a predetermined ordering of independent variables and corresponding dependent variables, wherein the predetermined ordering is dictated by a specific measurement being performed; and outputting the organized predetermined ordering to at least one computer readable medium.

23. The method of claim 22 further comprising the steps of:

limiting access to the organized predetermined ordering;

preventing modification of data and metadata corresponding to the organized predetermined ordering; and, documenting authorship of the organized predetermined ordering.

24. The method of claim 22 wherein the step of documenting authorship comprises the step of: recording an electronic signature in the at least one computer readable medium.

25. The method of claim 22 wherein the step of outputting the organized predetermined ordering comprises the step of: outputting a substantially accurate time and date indicator to the at least one computer readable medium.

26. A computer usable medium having computer readable code embodied therein, said computer readable code being capable of causing at least one processor to:

obtain data corresponding to at least one measurement obtained from an interaction between a sample and a collimated beam of electromagnetic radiation;

calculate characteristics from the obtained data;

organize the calculated characteristics in a predetermined ordering of independent variables and corresponding dependent variables, wherein the predetermined ordering is dictated by a specific measurement being performed; and store the organized predetermined ordering.

27. The computer usable medium of claim 26 wherein the computer readable code is also capable of causing said at least one processor to:

limit access to the organized predetermined ordering;

prevent modification of data and metadata corresponding to the organized predetermined ordering; and, document authorship of the organized predetermined ordering.

28. The computer usable medium of claim 26 wherein, in documenting authorship, said computer readable code is capable of causing said at least one processor to: record an electronic signature.

29. The computer usable medium of claim 26 wherein, in outputting the organized predetermined ordering, said computer readable code is also capable of causing said at least one processor to: output a substantially accurate time and date indicator.

30. A measurement apparatus comprising:

a source of electromagnetic radiation;

a first optical system capable of substantially collimating electromagnetic radiation;

an optical delivery system capable of providing electromagnetic radiation from said source to said first optical system;

a sample holding assembly capable of holding a sample and placing the sample in an optical path of the substantially collimated electromagnetic radiation;

a second optical system capable of receiving electromagnetic radiation transmitted through the sample and at least a portion of said sample holding assembly;

a detecting system capable of detecting electromagnetic radiation;

an optical transmission system capable of receiving electromagnetic radiation from said second optical system and transmitting the received electromagnetic radiation to said detecting system;

said second optical system being also capable of transmitting electromagnetic radiation to said optical transmission system;

said detecting system being optically disposed to receive electromagnetic radiation from said optical transmission system;

a data collector interface component operatively connected to said detecting system and capable of receiving data from said detecting system;

at least one processor;

at least one computer readable medium; and at least one other computer readable medium;

said at least one computer readable medium having computer readable code embodied therein, said computer readable code being capable of causing said at least one processor to:

receive data from said detecting system corresponding to a measurement, calculate characteristics from the received data, organize the calculated characteristics in a predetermined ordering of independent variables and corresponding dependent variables, wherein the predetermined ordering is dictated by a specific measurement being performed, and output the organized predetermined ordering to said at least one other computer readable medium;

said at least one processor, said at least one computer readable medium, said at least one other computer readable medium and said data collector interface component operatively connected to each other.

* * * * *